United States Patent [19]

Allington et al.

[11] Patent Number: 4,575,424

[45] Date of Patent: Mar. 11, 1986

[54] CHROMATOGRAPHIC FLOW CELL AND METHOD OF MAKING IT

[75] Inventors: Robert W. Allington; John N. Jones, both of Lincoln, Nebr.

[73] Assignee: ISCO, Inc., Lincoln, Nebr.

[21] Appl. No.: 585,347

[22] Filed: Mar. 1, 1984

[51] Int. Cl.$^4$ .............................................. B01D 15/08
[52] U.S. Cl. ..................... 210/198.2; 55/197; 73/61.1 C; 356/246; 422/70
[58] Field of Search ................ 55/197, 386; 73/23.1, 73/61.1 C; 210/198.2, 198.3; 356/246; 422/70, 81

[56] References Cited

U.S. PATENT DOCUMENTS

| | | | |
|---|---|---|---|
| 3,515,491 | 6/1970 | Emary | 356/246 |
| 3,518,008 | 6/1970 | Skeggs | 73/23.1 X |
| 3,524,709 | 8/1970 | Hrdina | 356/246 |
| 3,646,313 | 2/1972 | Gorgone et al. | 356/246 X |
| 3,684,386 | 8/1972 | Noll | 356/246 |
| 3,783,276 | 1/1974 | Allington | 250/226 |
| 3,934,965 | 1/1976 | Wiseman et al. | 356/246 |
| 3,941,487 | 3/1976 | Ehret et al. | 73/61.1 C X |
| 3,975,104 | 8/1976 | Munk | 356/246 |
| 4,006,990 | 2/1977 | Munk | 356/246 |
| 4,008,397 | 2/1977 | Zdrodowski | 356/246 X |
| 4,019,372 | 4/1977 | Parkell et al. | 73/61.1 C |
| 4,042,333 | 8/1977 | Dell et al. | 73/864.81 X |
| 4,074,940 | 2/1978 | Tarbet | 356/246 |
| 4,220,415 | 9/1980 | Staab et al. | 356/246 X |
| 4,343,767 | 8/1982 | Long et al. | 73/61.1 C X |
| 4,374,620 | 2/1983 | Berick et al. | 356/246 |
| 4,455,089 | 6/1984 | Yeung et al. | 356/246 X |
| 4,462,962 | 7/1984 | Baba et al. | 210/198.2 X |

OTHER PUBLICATIONS

Edward D. Black, "Potassium Bromide Capillary Cell for Infrared Microspectroscopy", Analytical Chemistry, No. 32, 1960.

Primary Examiner—Robert Spitzer
Attorney, Agent, or Firm—Vincent L. Carney

[57] ABSTRACT

To accommodate microscale chromatographs, a flow cell has an inlet port, inlet path, light path, outlet path and outlet port, with the inlet and outlet paths being formed continuously around wires of the proper diameters during molding. The wires pass through the mold and against a metal light-path insert during molding and are removed from the plastic after molding to form portions of the inlet and outlet paths. The insert for the light path is formed in two parts, each having a groove in the form of a half cylinder along its center for the light path and having channels on each side. The paths are machined prior to lapping, and after lapping, the light path is coated with a bright metal such as rhodium and then it is burnished for a mirror image with a roughness of less than sixteen RMS micro inches.

17 Claims, 15 Drawing Figures

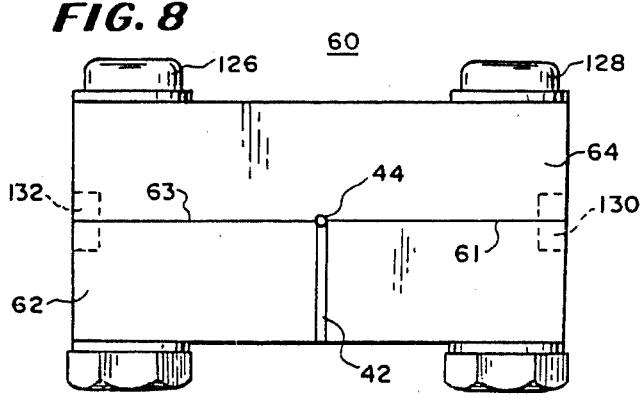
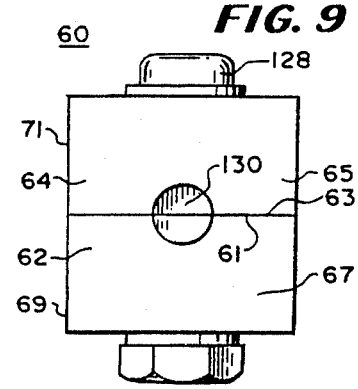
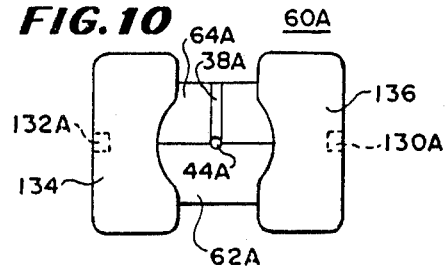
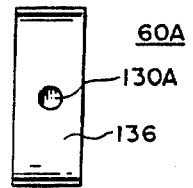
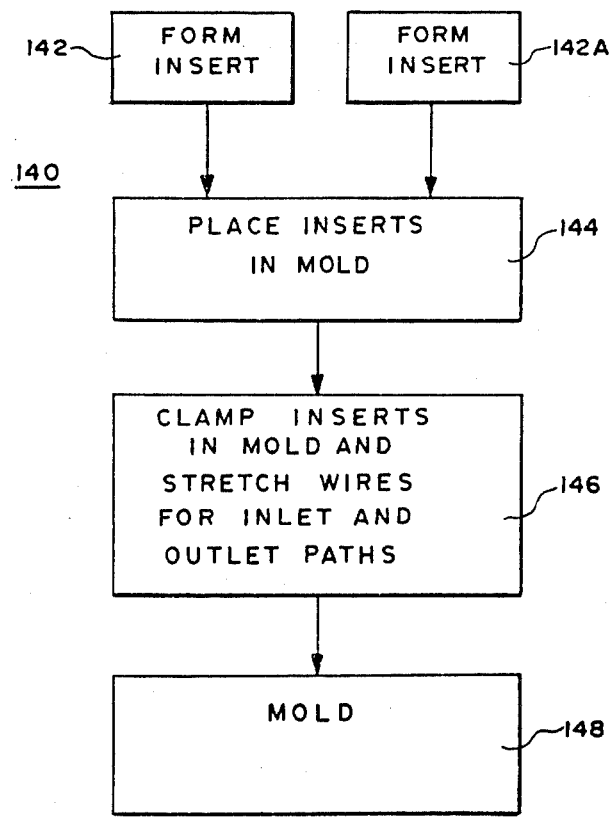

CHROMATOGRAPHIC FLOW CELL AND METHOD OF MAKING IT

BACKGROUND OF THE INVENTION

This invention relates to chromatography and more particularly to microscale chromatography.

Microscale chromatography includes the same apparatus on a very much smaller scale as high performance liquid chromatography. A common column diameter for micro liquid chromatography is one millimeter and a common conventional high performance liquid chromatography column diameter is 4.6 millimeters.

In the known microscale chromatographs, flow cells having a lower volume than conventional high pressure liquid chromatographs are used to monitor the eluate. These flow cells have viewing windows for transmitting light through a light path and have inlet and outlet paths.

In the prior art microliquid chromatographs, the flow paths through the flow cells have had large volumes and in one embodiment, the light path is a transmission path through a continuous straight diameter flow path between the inlet and outlet.

The prior art flow cells have several disadvantages such as: (1) they are difficult to fabricate; (2) they have had large volume resulting in bandspreading; and (3) they have not had desirable reflectivity and smoothness of the walls of the light path.

SUMMARY OF THE INVENTION

Accordingly, it is an object of the invention to provide a novel flow cell for liquid chromatography.

It is a further object of the invention to provide a novel method of making a flow cell.

It is a still further object of the invention to provide a flow cell having a light path with high reflectivity and low roughness.

It is a still further object of the invention to provide a technique for forming flow cells in which the continuous inlet path, light path and outlet path are formed in such a manner as to avoid misalignments, voids and blockages.

In accordance with the above and further objects of the invention, a flow cell includes a two part metal light-path insert with a light path formed between the two parts, half in one and half in the other, and being continued on opposite sides with: (1) the path on the inlet side of the light path continuing through the plastic portion of the flow cell to the flow cell inlet; and (2) the path on the outlet side of the light path through the plastic portion of the flow cell to the outlet port of the flow cell.

To form the flow cell, a different half of the light path is milled in each of the two stainless steel parts so they match together and, in one embodiment, paths are cut across one end of one of the parts and down the end of the other part, all of the paths being lapped. The wall of the two paths that are to form the light conducting path is then plated with a shiny metal such as rhodium and burnished so that it has a roughness factor of less than 16 RMS microinches and has a mirrorlike surface.

The flow cell is molded about the light-path insert with wires of the proper length placed near the light path between the two parts where they are held by window inserts. They extend down the sides of the light-path insert and are stretched across a mold to the inlet port insert and outlet port insert before plastic is molded around the inserts. After molding, the wires are removed to form a continuous inlet path from the inlet port to the light path and a continuous outlet path from the light path to the outlet port.

The lengths of the light paths in the preferred embodiment are one millimeter for the smallest lightpath insert and ten millimeters for the largest. The length of the inlet path is less than the product of the length of the light path and the fourth power of the diameter of the light path divided by the fourth power of the diameter of the inlet path. The inlet path is less than thirty and preferably less than fifteen millimeters in length.

From the above summary, it can be understood that the flow cell of this invention has several advantages, such as: (1) relatively small inlet diameter and short light and outlet paths are formed which are continuous and free from misalignments and pockets which may hold fluid from a previous peak; (2) the light path is less than thirty and preferably less than fifteen millimeters long and can be made less than one-half millimeter in diameter; (3) the light path is shiny with a mirror image and a roughness factor of less than 16 RMS micro inches; and (4) the flow cell is easily formed and inexpensive.

SUMMARY OF THE DRAWINGS

The above noted and other features of the invention will be better understood from the following detailed description when considered with reference to the accompanying drawings, in which:

FIG. 8 is an elevational view of a portion of the embodiment of FIG. 2;

FIG. 9 is an end elevational view of a portion of the embodiment of FIG. 2;

FIG. 10 is a plan view of the embodiment of FIG. 5;

FIG. 11 is an end view of the part of the embodiment of FIG. 5;

FIG. 12 is a flow diagram of a method in accordance with the invention;

DETAILED DESCRIPTION

Figure 1:
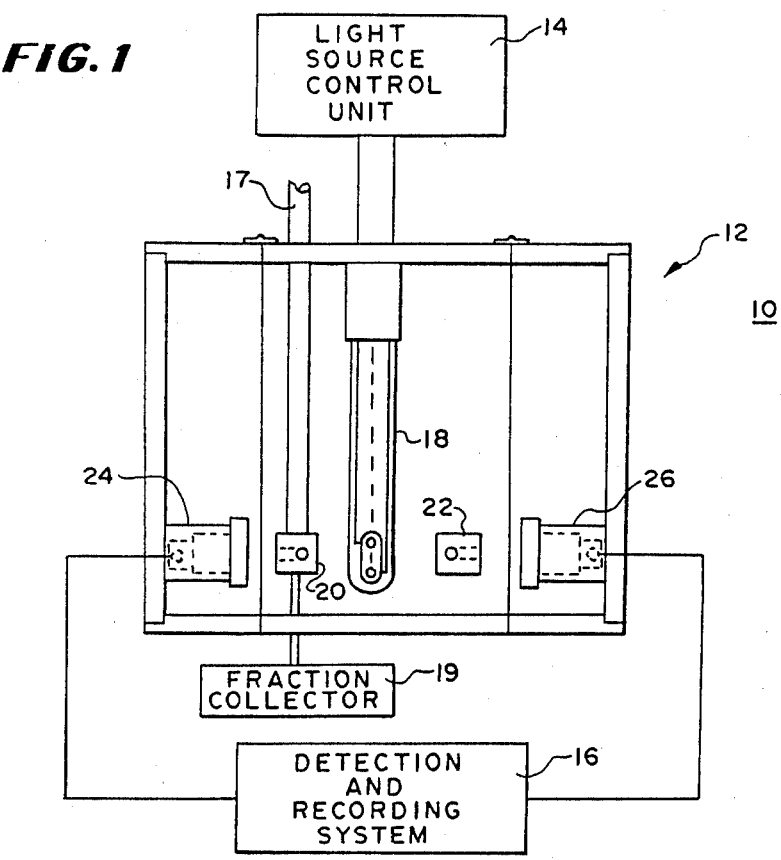
FIG. 1 is a fragmentary schematic drawing of a chromatograph including an embodiment of the invention.

In FIG. 1 there is shown a schematic view of liquid chromatograph 10 having, as its principal parts, a dual beam optical system 12, a light source control unit 14, a detection and recording system 16 and a chromatographic column 17. Two flow cells, 20 and 22, are within the dual beam light source 12 adapted to receive light therethrough for the generation of signals to be applied to the detection and recording system 16.

The flow cell 20 is connected to the chromatographic column 17 to receive fluid therefrom and permit its flow therethrough to a fraction collector 19 and the flow cell 22 is positioned to monitor a standard fluid for the detection of signals to be compared with signals representing the fluid passing through the flow cell 20.

The dual beam light source 12 has, as its principal parts, a lamp 18, first and second flow cells 20 and 22 and first and second photocells 24 and 26 arranged so that the lamp 18 emits light which is focused through the flow cells 20 and 22 onto the photocells 24 and 26.

The light passing from the lamp 18 through the flow cells 20 and 22 is converted to electrical signals in the photocells 24 and 26 which signals are applied to the detecting and recording system 16 to determine the light absorbance of the solution and thus provide information, usually in the form of chromatographic peaks indicating the nature of the substances in the fluid. Such a dual beam optical system 12 is described more fully in U.S. Pat. No. 3,783,276, the disclosure of which is incorporated herein by reference.

Figure 2:
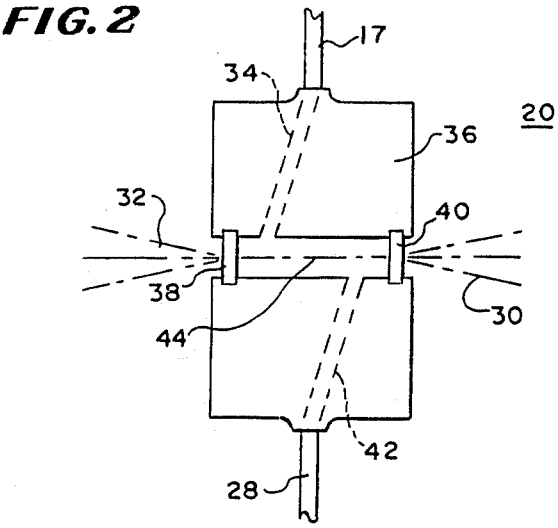
FIG. 2 is a simplified elevational drawing of a portion of FIG. 1.

In FIG. 2 there is shown a simplified, enlarged view of the flow cell 20 directly connected at its upper end and receiving within it the end of the liquid chromatographic column 17 and at its bottom and an eluate outlet 28 which may lead to the fraction collector 19 (FIG. 1). Light indicated schematically at 30 enters the flow cell 20 to flow through the fluid therein and be emitted as shown schematically at 32 for application to the photocell 24 (FIG. 1). The chromatographic column 17 is shown schematically but includes the usual accessories such as a sample injection valve for applying samples to the chromatograph for analysis and a high pressure eluant inlet from a source of eluant.

The chromatograph itself may be of any type but in the preferred embodiment it is directed to a microscale, high performance liquid chromatograph such as that described in co-pending U.S. patent application 300,567 filed by Robert W. Allington on Sept. 9, 1981 and assigned to the same assignee as this application, the disclosure of which is incorporated herein by reference. Such microliquid chromatographs are a form of high performance liquid chromatographs that differ from conventional high performance liquid chromatographs in that the inside diameter of the microscale chromatographic column 17 is substantially less than the usual four to five millimeters of the conventional column and for the purposes of this description is less than two millimeters.

A common column diameter for micro liquid chromatography is one millimeter and a conventional high performance liquid chromatography column diameter is 4.6 millimeters. Thus, the cross-sectional area of a micro liquid chromatography column is about 1/20 that of a high pressure liquid chromatography column and so micro liquid chromatography solute peaks are smaller in volume by at least a factor of 20. It is more than a factor of 20 if the length of a peak residing in the column also decreases when going from high pressure liquid chromatography to micro liquid chromatography.

The fluid from the chromatographic column 17 must flow through a narrow diameter inlet path 34 within the body assembly 36 of the flow cell 20. At the bottom of the narrow diameter inlet path 34. the fluid flows in a horizontal path between window assemblies indicated schematically at 38 and 40 which form windows for the light 30 to pass through. At the forward end of this path, is an angled, downwardly-extending, outlet path 42 which leads into the conduit 28.

Because the flow paths through the chromatographic column 17, the narrow diameter inlet path 34, the light path 44, which is horizontal and the outlet path 42 are of such small diameters, it is difficult to have a clean path with connections that do not leak excessively. Moreover, the light path 44 between the windows and the window assemblies 38 and 40 must be polished and smooth to avoid excessive loss due to absorbance and wave guide loss and avoid noise in the light transmitted along light path 44.

Figure 3:
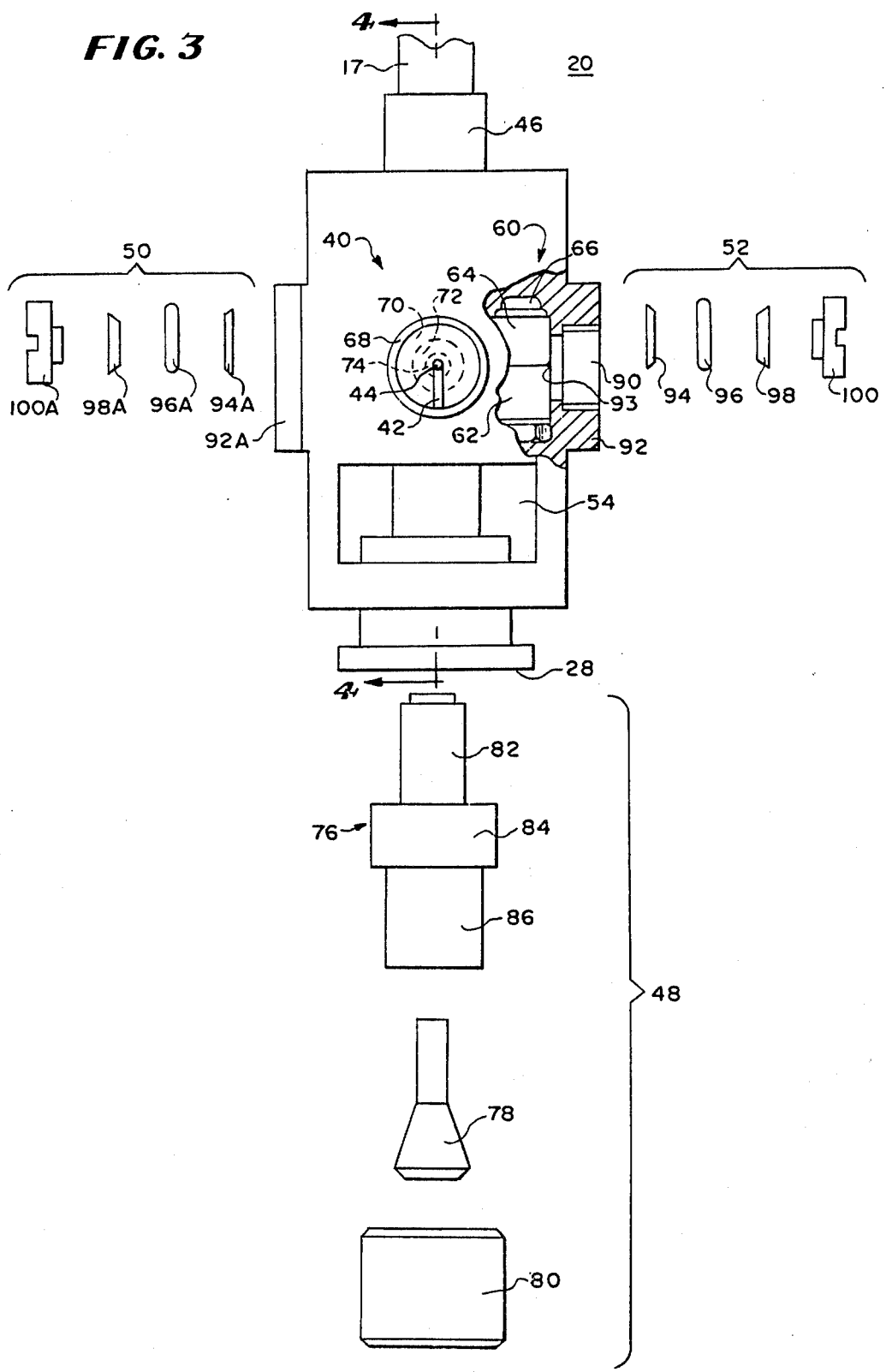
FIG. 3 is an elevational drawing, partly broken away and partly exploded of the part shown in FIG. 2.

In FIG. 3, there is shown a side elevational view, partly broken away and exploded of the body assembly 36. The body assembly 36 includes an inlet port assembly 46, an outlet port assembly 48, two window assemblies, one of which is shown at 40, first and second mounting ports 50 and 52 and a release recess 54.

To provide a flow path aligned with the window assemblies 40 (FIGS. 2 and 3) and 38 (FIG. 2), a light-path insert 60 includes within it the light path 44 (FIG. 2) connected at one end to the narrow diameter inlet path 34 (FIG. 2) and at the other end to the outlet path 42. This light-path insert 60 includes a top and bottom portion 62 and 64 held together by bolts, one of which is shown at 66 and having the light path 44 between them.

To admit light to the flow cell 20, the window assembly 40 includes a window insert 68, a window nut 70, an O ring 72 and a quartz window 74 in that order from the outside to the inside of the window assembly. A backup washer is also between the window nut 70 and the O ring 72 but is not shown in FIG. 3. The window insert 68 is molded within the plastic housing to receive the window nut 70 which is threaded therein to depress the backup washer (not shown in FIG. 3) and the O ring 72 against the quartz window 74. This structure provides a liquid tight seal but still transmits light to the light path 44 at the top of the outlet path 42 and thus permits light to pass through the flow cell 20.

To receive the chromatographic column 17, the inlet port assembly 46 of the flow cell 20 communicates at its lower end with the inlet path 34 (FIG. 2) and the oulet port assembly 48 communicates at the lower end of the outlet path 42. The outlet port assembly 48 includes a connector 76, a mounting fixture 78 and a column holding nut 80 in the order described from the flow cell 20 outward to the chromatographic column 17. The communication between the column 17 and the flow cell is described in the copending application to John N. Jones, Abolghassem Y. Tehrani and Robert W. Allington, filed concurrently herewith, entitled "Apparatus for Reducing Tailing in a Liquid Chromatograph," the description of which is incorporated by reference.

The connector 76 has a narrow stem 82 adapted to mount within the flow cell 20 and connected by a shoulder to a ring 84 which terminates in a sleeve 86 adapted to receive the narrow stem of the conduit mounting fixture 78. The mounting fixture 78 is held in place by the holding nut 80 and the connector 76 threads within the flow cell 20 in a manner known in the art to connect a conduit thereto.

To hold the light-path insert 60 in place during molding of the flow cell 20, the light-path insert 60 has on each end, at a central location, a centering recess, one of which is shown at 90 and the body assembly 36 (FIG. 2)

has a boss 92 on one side and a corresponding boss 92A on the other side, the two bosses being identical, internally threaded and adapted to expose centering detents such as the one at 93 in the recess 90 for holding the light-path insert 60 in place and sealing it against fluid flow. Centering detents are centered in the sides of the inserts, one of which is shown at 93, and are used in the molding process.

The bosses 92 and 92A, each receive a corresponding one of the sealing cylindrical gaskets 94 and 94A of a deformable material such as TEFLON, "O"rings 96 and 96A, backup washers 98 and 98A and nuts 100 and 100A adapted to fit in the order described to seal the flow cell 20 during use. With this arrangement, the mounting ports 50 and 52 are used to mold the flow cell 20 in a manner to be described hereinafter and may later be sealed against the flow of fluid therethrough.

Figure 4:
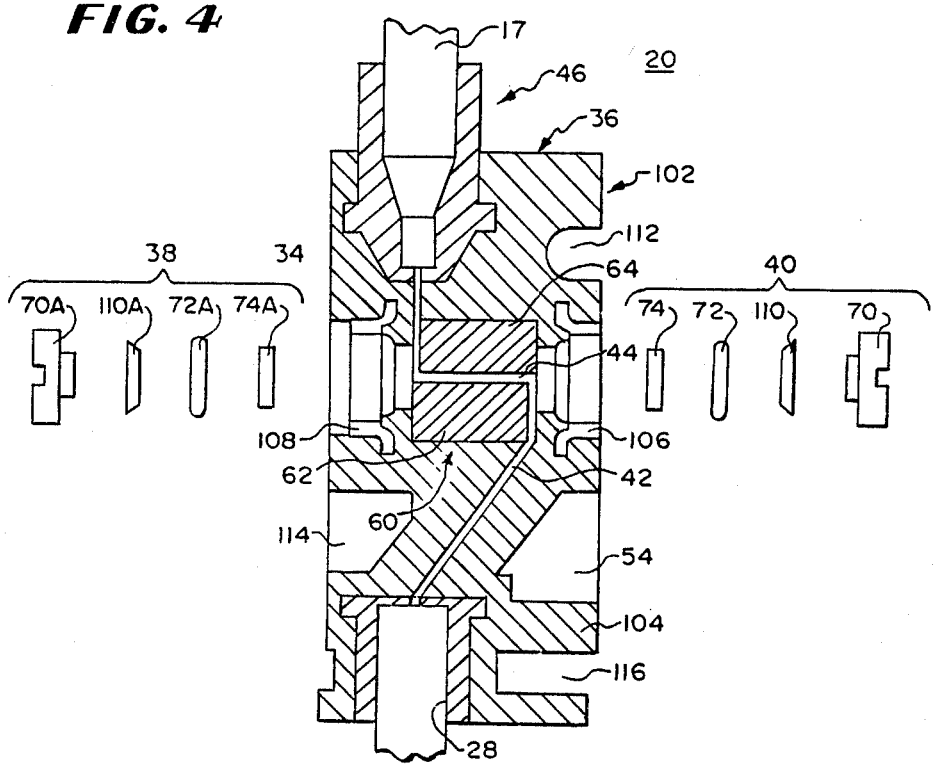
FIG. 4 is a longitudinal section of the part shown in FIG. 2 with portions exploded.

In FIG. 4 there is a longitudinal sectional view of the flow cell 20 taken through lines 4—4 of FIG. 3 showing the inlet, outlet and light-paths 34, 42 and 44 respectively, an upper plastic portion 102, the light-path insert 60 and a lower plastic portion 104. The inlet path 34 extends from the inlet port assembly 46 through the upper plastic portion 102 and along one side of the top portion 64 of the light-path insert 60 to a central location where it communicates with one end of the light path 44 between the top and bottom portions 64 and 62 of the light-path insert 60. The outlet path 42 extends down the opposite side of the bottom section 62 of the light-path insert 60 and into the outlet path at 42. It extends from there down to the conduit 28. While the inlet and outlet paths are shown partly machined in the light-path insert 60, they may be formed to a greater or lesser extent.

To permit the passage of light through the light path 44, the window assemblies 38 and 40 are substantially identical and each include cylindrical recesses having a center aligned with the center of the light path 44 to permit light to pass therethrough. Each has a different outer cylindrical window inserts 106 and 108 formed of metal and being internally threaded and molded in the upper and lower plastic portions 102 and 104 surrounding the longitudinal axis that is aligned with the outlet path 42 for the window assemblies 40 and 38 respectively.

The inner diameter of each of the window inserts is 0.260 inch and each extends straight inwardly about the longitudinal axis to a shoulder which forms a second cylinder having a diameter of 0.220 inch until it approaches the outlet path 42. The window assembly 40 receives a quartz window 74 approaching the path, an "O"ring 72 within the shoulder, a backup washer 110 and the window nut 70 in the order named and the window assembly 38 receives a similar quartz window 74A abutting the other end of the outlet path 42 against the light-path insert 60, the "O"ring 72A, a backup washer 110A and the window nut 70A. With this arrangement, the windows are held in place against opposite sides of the light-path insert 60 to permit light to pass through the outlet path 42.

To connect a chromatographic column 17 to the inlet port 46, the inlet port 46 is a cylindrical fitting molded within the upper plastic portion 102. It has a substantially conical cylindrical cross-section narrowing adjacent to the inlet path 34 to a diameter corresponding to that of the end of the chromatographic column 17. The outlet path 42 is approximately twice the diameter of the inlet path 34.

The lengths of the light paths in the preferred embodiment are one millimeter for the smallest light-path insert and ten millimeters for the largest. The length of the inlet is less than the product of the length of the inlet path and the fourth power of the diameter of the light path divided by the fourth power of the diameter of the inlet path. The inlet path is less than twenty-five and preferably less than fifteen millimeters in length.

To mount the flow cell 20 in place in the light monitor of the chromatographic system, a curved groove having a radius of 0.16 inch is formed one-quarter of an inch from the top surface of the upper plastic portion 102 as shown at 112. A yolk fits within this groove to hold the flow cell 20 in place with respect to the lamp 18 (FIG. 1) and the detectors 24 and 26 (FIG. 1). To reduce the thickness of the plastic about the paths and thus reduce voids in the plastic adjacent to inlet path 34 and outlet path 42 and other distortions caused in molding the plastic, second and third recesses are formed at 54, 114 and 116 with the recesses at 54 and 114 being shaped to maintain a substantially constant cross-section about the plastic surrounding a portion of the outlet path 42.

Figure 5:
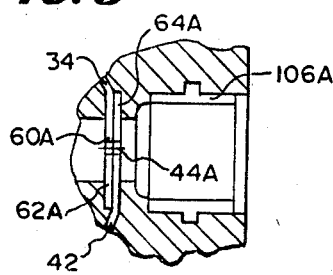
FIG. 5 is a sectional view of another embodiment of the part shown in FIG. 2 illustrating the differences between the embodiments.

In FIG. 5 there is shown a sectional view of another embodiment of light-path insert 60A which differs from the light-path insert 60, primarily in being adapted for use with a small column. This flow cell has a shorter light path 44A, such as a one millimeter long light path formed between top and bottom parts 62A and 64A of the insert than the light path 44 which may be 5 or 10 millimeters long. Because of its narrower width, the window insert 106A is shaped differently to grip the plastic parts better. The length of the light paths 44A or 44 is determined by balancing the need for higher concentrations of sensitivity and the resolution.

Figure 6:
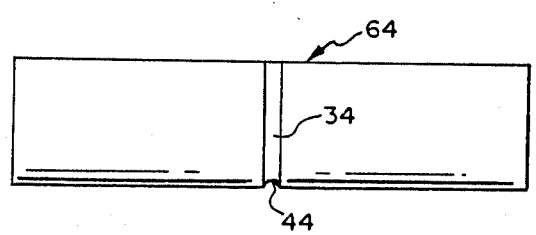
FIG. 6 is an elevational view of a portion of the embodiment of FIG. 2.

In FIG. 6, there is shown an elevational view of the top portion 64 of the light-path insert 60. As shown in this view, a downwardly extending groove 34 is provided which communicates at its bottom end with the light path 44 (FIG. 4) and forms a part of the inlet path 34, matching with the portion of the path within the upper plastic portion 102 (FIG. 4). The metal insert is 2/10 of an inch in height and is preferably of stainless steel although it may be of any suitable material for handling the eluant. During molding of the flow cell, a wire lies in this path and is, after molding, removed to form the inlet path 34.

Figure 7:
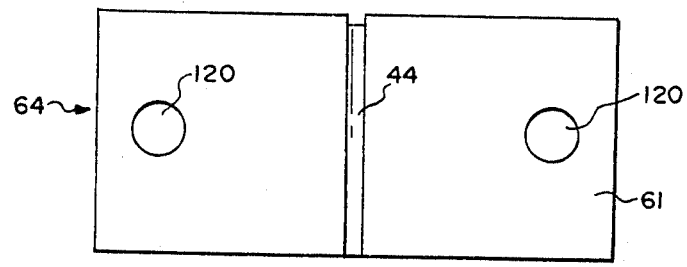
FIG. 7 is a bottom view of the part of FIG. 6.

In FIG. 7, there is shown a bottom view of the top portion 64 which is of stainless steel and has a width of 0.3937 inch for the 10 millimeter light path and a length of 0.840 inch, with first and second bolt holes 120 and 122 spaced apart about the centered half cylindrical light path 44. This light path meets a second half on top of the bottom portion 62 (FIG. 4) to which it is bolted so as to form a cylinder having a diameter of less than one millimeter and constituting the light path 44 extending in a direction perpendicular to the 0.840 inch length and parallel to the dimension which is the 0.3937 inch width. The light path 44 has a diameter larger than the inlet path 34 and no larger than the outlet path 42. In the preferred embodiments for five and ten millimeter long light paths, the diameters are one-quarter millimeter and for the one and two millimeter long light paths, the diameter is one-fifth millimeter.

The bottom portion 62 (not shown in FIG. 7) has the outlet path 42 extending downwardly from the opposite end of the light path 44 and meeting with the portion of the outlet path 42 that is within the lower plastic portion 104 (FIG. 4). The outlet path 42 in the preferred embodiment is equal in diameter to the light path 44 and twice the diameter of the inlet path 34.

The light path 44 is formed by milling the appropriate size groove, plating with bright rhodium and burnishing. It is burnished to a finish which is mirror in quality and smoother than a 16 RMS microinch finish. Preferably, it is a 4 RMS microinch finish. While rhodium is used in the preferred embodiment, any plating which provides a suitably smooth bright mirrorlike finish and is corrosion resistant may be used. The sides of the upper and lower plates 62 and 64 are lapped on mating surfaces and surfaces receiving the window inserts.

In FIG. 8 there is shown an assembled light-path insert 60 having the top portion 64 and the bottom portion 62 mounted together and held in place by the bolts 126 and 128 with a channel for the outlet path 42 being cut down the bottom portion 62 from the light path at 44 to receive fluid from the light path 44 (FIG. 4). The outlet path 42 is similar to the inlet path 34 (FIG. 4) except it may be larger. The bolts 126 and 128 hold the top and bottom portions 62 and 64 together in close registration.

The lapped surfaces 61 and 63 of the upper and lower portions 64 and 62 are held in close registration in a clamping relationship. As best shown in FIG. 9, the sides of the top and bottom portions 64 and 62 of the light-path insert 60 parallel to both the bolts 128 and the light path 44 (FIG. 4) have centering detents in them with the centering detent 130 being shown in FIG. 9. This detent 130 is aligned with a centering detent 132 (FIG. 8). These two detents are adapted to meet fixtures which center the light path insert 60 during molding of the flow cell 20 and thus help align in colinear relationship the top and bottom portions 62 and 64 during molding to form a more perfect light path. The surfaces 65 and 71 of the top part 64 are perpendicular to the light path 44 and colinear with the surfaces 67 and 69 respectively of the lower part 62.

In FIG. 10 there is shown a short light-path insert 60A having a bottom part 62A and a top part 64A, with a portion of the inlet path 38A being milled in the top part 64A to reach the light path 44A, which is milled and finished in the top and bottom parts 64A and 62A. On each end, are the centering detents 132A and 130A.

Because the short light-path inserts are narrow, their upper and lower parts cannot be bolted end-to-end with reliability and for that reason, are held together by plastic parts molded onto them as shown at 134 and 136. As shown in FIG. 11, the molded part 136 contains the centering detent 130A and is substantially wider than twice the width of the top and bottom parts 62A and 64A and has a width of one-quarter of an inch and a height of 0.6 inch.

In FIG. 12 there is shown a flow diagram 140 illustrating the general steps taken to fabricate the flow cell 20 (FIGS. 1-4) which are: (1) the steps 142 and 142A of forming the inserts; (2) the step 144 of placing the inserts in a mold; (3) the step 146 of clamping the inserts in the mold and stretching the wires for the inlet and outlet paths; and (4) the step 148 of injecting plastic to mold the flow cell 148. In the preferred embodiment, the plastic is polypropylene with 10 percent glass fibers. The plastic granules and/or the inserts receive a coupling agent for better adhesion to the metal parts.

In addition to the light-path insert 60, there are the window inserts 106 and 108 (FIG. 4) and the inlet and outlet inserts 46 and 28. They are all placed in the mold and clamped in place. The clamping is accomplished by four anvils which screw in the sides of the molds. The wires are positioned against the light-path insert 60 during molding and stretched into the inlet and the outlet mold parts so that, when the plastic flow cell is formed, the wires form passages in the plastic to the light-path insert. The wires are held in place against the light-path insert during molding by one pair of mold anvils onto which the windows are screwed. The other pair screw into the mold in a perpendicular direction and stick into the detents. The wire for the inlet path is one half the diameter of the light path and the wire for the outlet path.

Figure 13:
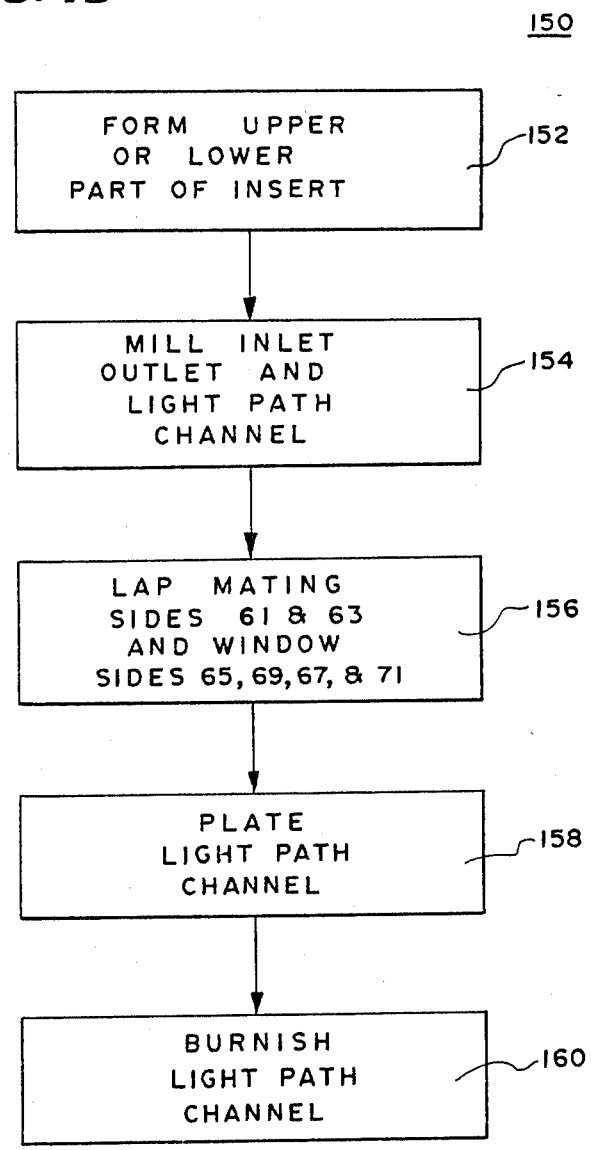
FIG. 13 is a flow diagram of a step shown in the flow diagram of FIG. 12.

In FIG. 13 there is shown a flow diagram 150 illustrating the formation in general terms of the inserts and having: (1) the step 152 of forming upper and lower parts of the insert with holes for bolding; (2) the step 154 of milling the inlet and the outlet and the light paths and burning the light paths; (3) the step 156 of lapping the mating sides 61 and 63 and window sides 65, 69, 67 and 71 in pairs; (4) the step 158 of plating at least the light paths with rhodium or another reflective material and (5) the step 160 of burnishing the light paths.

Figure 14:
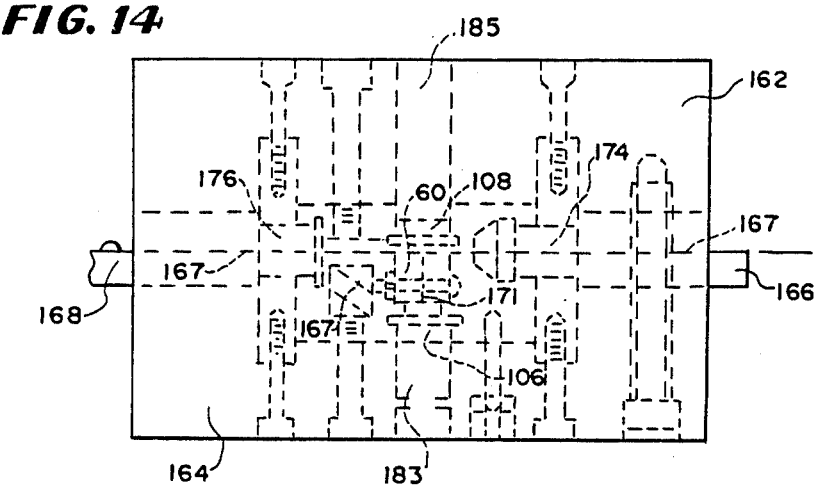
FIG. 14 is a plan view of the apparatus used in practicing the invention.

After the paths have been burnished, the parts are mounted together and, in the case of flow cells for larger columns, the two parts are bolted together. In the case of smaller flow cells, the two insert parts are molded together in a manner to be described hereinafter to hold them with a proper path between them. Of course, the holes mentioned in step 152 are not needed. In FIG. 14 there is shown a plan view of the mold for forming the flow cell having an upper mold part 162, a lower mold part 164, wires 167 extending from the mold parts for the inlet end 166 through the light channel at 171 and for the outlet end at 168, fastened in place to form the continuous inlet, outlet and light paths. As shown in hidden lines, the window inserts 106 and 108 are mounted on anvils 183 and 185 on either side of the light-path insert 60. The mold also received the inlet insert 146 and the exit insert 128 to be formed integrally of the plastic about the insert. The anvils cooperate with perpendicular anvils to hold the light path.

Figure 15:
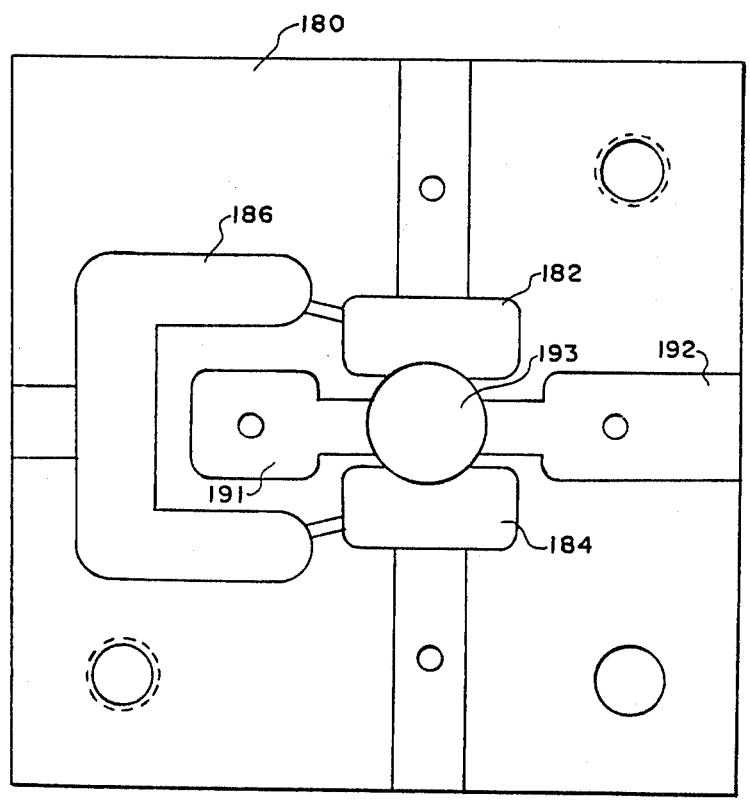
FIG. 15 is another embodiment of the apparatus for making the invention shown in FIG. 14.

In FIG. 15 there is shown another mold part 180 which cooperates with a mating part to form the smaller insert 60A (FIGS. 10 and 11) with the plastic end portions 134 and 136 being formed in cavities 182 and 184 to hold the insert parts 62A and 64A (FIGS. 9 and 10) together with plastic from the runners 186. During molding of the flow cell 20 about the insert 60A, anvils clamp the upper and lower parts 62A and 64A with two anvils moving in the areas 191 and 192 and two other circular anvils from perpendicular directions meeting at the area 193 are moved against the sides of the insert portions 62A and 64A to hold them in place about the wires during the molding operation and thus insure proper alignment.

From the above description, it can be understood that the flow cell of this invention and the method of making it have several advantages, such as: (1) continuous unobstructed inlet, light and outlet paths are formed of sufficiently small diameter to accommodate flow from microscale chromatographic columns; (2) the light path is extremely bright having a mirror reflective surface and a finish better than 16 RMS micro inches in spite of the difficulty of making extremely small diameter light paths of less than two millimeters; and (3) the process of making it is relatively economical since the paths are formed and kept clear by the wire during the molding process.

Although a preferred embodiment of the invention has been described with some particularity, many modifications and variations may be made without deviating from the above description. Therefore, it is to be understood that, within the scope of the appended claims, the invention may be practiced other than as specifically described.

What is claimed is:

1. A method of making a flow cell for a chromatographic column having an inner diameter of less than two millimeters comprising the steps of:
   forming first and second insert parts of stainless steel in the shape of matching parallelopipeds with matching surfaces and perpendicular end sections;
   milling in each of the matching surfaces, a channel having a diameter less than four millimeters;
   milling smaller paths in the end section of one of said first and second members in a first direction and the other in a second direction;
   lapping said paths to form a smoother surface;
   plating the paths in said matching surfaces of said first and second members with a reflective metal;
   burnishing said reflective metal;
   placing one end of a first wire, having a diameter corresponding to the diameter of said chromatographic column near one end of the paths on said matching surfaces and stretching said first wire through a mold for plastic into an inlet port section of said mold;
   placing one end of a second wire having a diameter twice the diameter of the first wire near a second end of the paths on said matching surfaces and stretching said second wire into an outlet port with inserts for windows being positioned aligned with the ends of said path and said matching surfaces;
   said first wire extending less than fifteen millimeters within said mold;
   molding said flow cell with plastic so that said window inserts are aligned with said paths and hold said one end of said first wire and said one end of said second wire in place;
   removing said wire; and
   inserting said window parts into said insert, whereby a reflective light path aligned with the windows is provided between the inlet for chromatographic column and the outlet of the flow cell.

2. A method according to claim 1 in which the step of milling includes the step of milling a path less than one-half of a millimeter deep, two millimeters in diameter and of a length less than the length of said first wire in the mold multiplied by the fourth power of the diameter of the path and divided by the fourth power of the diameter of the first wire.

3. A method according to claim 2 in which the step of milling includes the step of milling a path less than one hundred times the diameter of the column.

4. A method of forming a flow cell for a chromoatograph having a chromatographic column of predetermined inner diameter less than two millimeters, comprising the steps of:
   forming two parts of a two part channel insert;
   machining a channel in at least one of said parts;
   attaching said two parts together to form a single channel insert;
   placing said insert in a plastic mold and stretching a first length of wire from said channel to an inlet portion and a second length of wire from said channel to an outlet portion of said mold;
   applying at least one window insert to said mold aligned with said channel between said two parts, whereby a window insert is molded in place for a flow cell window;
   inserting plastic in said mold, whereby a flow cell is formed partly of metal and partly of plastic; and
   removing said flow cell from the mold and removing the first and second lengths of the wire from said flow cell.

5. A method according to claim 4 in which said step of forming two parts of a two part insert includes the step of forming first and second insert parts of stainless steel in the shape of matching parallelopipeds with matching surfaces and perpendicular end sections.

6. A method according to claim 5 in which the step of machining a channel includes the steps of:
   machining in each of the matching surfaces, a channel having a diameter less than four millimeters;
   machining smaller channels in the end section of one of said first and second members in a first direction and the other in a second direction;
   lapping said channels to form a smoother surface;
   plating the channels in said matching surfaces of said first and second members with a reflective metal; and
   burnishing said reflective metal.

7. A method according to claim 4 in which the step of machining a channel includes the steps of:
   machining in each of the matching surfaces, a channel having a diameter less than four millimeters;
   machining smaller channels in the end section of one of said first and second members in a first direction and the other in a second direction;
   lapping said channels to form a smoother surface;
   plating the channels in said matching surfaces of said first and second members with a reflective metal; and
   burnishing said reflective metal.

8. A chromatograph comprising:
   a chromatographic column;
   an injection valve;
   a source of light;
   a flow cell;
   a photocell;
   a detection system connected to said photocell to receive light from said light source passing through said flow cell;
   said chromatographic column having a predetermined inside diameter no greater than two millimeters and communicating with said flow cell whereby said fluid from said chromatograph flows through said flow cell while said light passes through said flow cell;
   said flow cell having a plastic body portion; a metal insert; a pair of window inserts; an inlet port; a pair of windows and an outlet port;
   said metal portion being comprised of first and second parts with a path between said first and second parts having a diameter no greater than four millimeters, having a mirror reflective finish with a roughness factor no greater than 16 RMS microinches; and
   said pair of windows being aligned with said path.

9. A chromatograph according to claim 8 in which the outlet of the column is connected to the channel by a path of less than fifteen millimeters.

10. A chromatograph according to claim 9 in which the path has the same diameter as the inside diameter of the column with a tolerance of less than 25%.

11. A chromatograph according to claim 10 in which the channel has a roughness of approximately four RMS microinches.

12. A flow cell for a chromatograph comprising:
a plastic body portion;
a metal insert;
a pair of window inserts;
a pair of windows corresponding to said pair of window inserts;
an inlet port;
an outlet port;
said metal insert being comprised of first and second parts;
an insert channel between said first and second parts having a diameter no greater than two millimeters, having a mirror reflective finish with a roughness factor no greater than 16 RMS microinches;
said pair of windows being aligned with said insert channel;
said insert channel communicating with said plastic portion at its outer ends;
an inlet channel having internal walls within said plastic connecting one end of said insert channel to said inlet port; and
an outlet channel having internal walls in said plastic connecting the other end of said insert channel to said outlet port.

13. A chromatograph having a column with a column inlet and column outlet, said chromatograph including the flow cell of claim 12 in which the outlet of the column is connected to the insert channel by a path of less than fifteen millimeters.

14. A chromatograph according to claim 13 in which the path has the same diameter as the inside diameter of the column with a tolerance of less than 25%.

15. A chromatograph according to claim 14 in which the insert channel has a roughness of approximately four RMS microinches.

16. A mold for making a flow cell comprising:
a first mold part;
a second mold part;
said first and second mold parts including a cavity adapted to hold a metal insert;
means for holding a wire adjacent to said metal insert in said cavity;
means within said cavity for holding an inlet port;
means for holding an outlet port;
said means for holding said wire including means for holding said wire so it passes from said metal insert to said inlet port and to said outlet port;
window insert holding means; and
said window insert holding means being connected to mount window inserts adjacent to said metal insert.

17. A mold according to claim 16 including means for holding a first wire between said insert and said inlet port and a second wire between said insert and said outlet port.

* * * * *